(12) United States Patent
Huang et al.

(10) Patent No.: US 8,912,222 B2
(45) Date of Patent: Dec. 16, 2014

(54) METHOD TO CONTROL INSECTS RESISTANT TO COMMON INSECTICIDES

(71) Applicant: Dow AgroSciences LLC, Indianapolis, IN (US)

(72) Inventors: Jim X. Huang, Carmel, IN (US); Richard B. Rogers, Mobile, AL (US); Nailah Orr, Carmel, IN (US); Thomas C. Sparks, Greenfield, IN (US); James M. Gifford, Lebanon, IN (US); Michael R. Loso, Carmel, IN (US); Yuanming Zhu, Carmel, IN (US); Thomas Meade, Zionsville, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 262 days.

(21) Appl. No.: 13/717,771

(22) Filed: Dec. 18, 2012

(65) Prior Publication Data

US 2013/0123307 A1 May 16, 2013

Related U.S. Application Data

(60) Division of application No. 13/081,886, filed on Apr. 7, 2011, now Pat. No. 8,362,046, which is a continuation of application No. 11/704,824, filed on Feb. 9, 2007, now abandoned.

(60) Provisional application No. 60/815,932, filed on Jun. 23, 2006.

(51) Int. Cl.
| | | |
|---|---|---|
| *A01N 43/40* | (2006.01) | |
| *A01N 43/10* | (2006.01) | |
| *A01N 43/18* | (2006.01) | |
| *A01N 43/80* | (2006.01) | |

(52) U.S. Cl.
CPC .............. *A01N 43/40* (2013.01); *A01N 43/10* (2013.01); *A01N 43/18* (2013.01); *A01N 43/80* (2013.01)
USPC ........................................................ 514/357

(58) Field of Classification Search
USPC ........................................................ 514/357
See application file for complete search history.

(56) References Cited

U.S. PATENT DOCUMENTS

| | | |
|---|---|---|
| 2005/0228027 A1 | 10/2005 | Zhu et al. |
| 2007/0203191 A1 | 8/2007 | Loso et al. |
| 2008/0033180 A1 | 2/2008 | Renga et al. |
| 2008/0058390 A1 | 3/2008 | Loso et al. |
| 2008/0108665 A1 | 5/2008 | Huang et al. |
| 2008/0108666 A1 | 5/2008 | Loso et al. |
| 2008/0108667 A1 | 5/2008 | Zhu et al. |
| 2008/0132705 A1 | 6/2008 | Heller et al. |
| 2008/0194634 A1 | 8/2008 | Arndt et al. |
| 2008/0194830 A1 | 8/2008 | Meyer et al. |
| 2008/0280915 A1 | 11/2008 | Loso et al. |

FOREIGN PATENT DOCUMENTS

WO    WO 2006/060029 A2    6/2006

*Primary Examiner* — Audrea Buckley
(74) *Attorney, Agent, or Firm* — Carl D. Corvin

(57) ABSTRACT

N-Substituted sulfoximines are effective at controlling insects resistant to common insecticides.

2 Claims, No Drawings

METHOD TO CONTROL INSECTS RESISTANT TO COMMON INSECTICIDES

This application claims the benefit of U.S. Provisional Application Ser. No. 60/815,932 filed on Jun. 23, 2006, and the benefit of U.S. non-provisional application Ser. No. 11/704,824 filed on Feb. 9, 2007, now abandoned, and the benefit of U.S. non-provisional application Ser. No. 13/081,886 filed on Apr. 7, 2011, now allowed.

BACKGROUND OF THE INVENTION

The present invention concerns a novel method to control certain insect pests, specifically those that have developed resistance to one or more classes of insecticides, through the use of N-substituted sulfoximines.

The development of resistance to insecticides in insect populations is a well recognized phenomenon and there are well documented cases of resistance for all of the major classes of insecticides (Georghiou and Saito, 1984 *Pest Resistance to Pesticides*. Plenum Press, New York; Whalon et al., 2007 *Arthropod Pest Resistance Database*, http://www.cips.msu.edu/resistance.rmdb). The reduction in effectiveness of insecticides due to the development of resistance is one of the forces that drives the discovery and development of new insecticides.

Predicting whether or not a resistance mechanism that has conferred resistance to an existing insecticide will confer resistance to a novel insecticide (i.e., cross-resistance) is not necessarily a simple matter. In the case where resistance is conferred by a change or modification in the molecular target at which the insecticide acts (i.e., target-site resistance), a novel insecticide that acts at a different target site is unlikely to be affected by the resistance mechanism. Thus, in such a case in which the target site at which a novel chemistry acts is known and the resistance mechanism of concern involves a modification to a different target site, one could predict with some confidence that the resistance mechanism would not confer resistance to the novel chemistry.

In contrast to the above, the case where the target site of the novel chemistry is not known or where resistance is conferred by some mechanism other than target site insensitivity (e.g., metabolic detoxification, sequestration, or excretion), cross resistance is difficult to predict. In these cases, empirical assessment of the cross-resistance among insecticide chemistries using well characterized resistant populations or "strains" of a target pest species provides the most direct and compelling evidence for the likelihood of cross-resistance One of the newer and more successful classes of insecticides to be introduced in past 25 years is the neonicotinoids. The introduction of neonicotinoid insecticides has provided growers with invaluable new tools for managing some of the world's most destructive crop pests, including species with a long history of developing resistance to earlier-used products. Imidacloprid was the first major active ingredient of the neonicotinoid class to reach the market. Research on molecules with a similar structure containing the 6-chloro-3-pyridylmethyl moiety led to acetamiprid, nitenpyram and thiacloprid. The substitution of the chloropyridinyl moiety by a chlorothiazolyl group resulted in a second subgroup of neonicotinoid insecticides including clothianidin and thiamethoxam.

Although the neonicotinoids have proved relatively resilient to the development of resistance, high levels of resistance have been documented in field-collected populations of the whitefly, *Bemisia tabaci*. During the late 1990s, resistant species increased in potency with more recently-collected strains of this whitefly exhibiting more than 100-fold resistance to imidacloprid, and comparable levels of resistance to thiamethoxam and acetamiprid (Elbert and Nauen, 2000 *Pest Manag Sci.* 56: 60-64; Rauch and Nauen, 2003 *Arch Insects Biochem Physiol.* 54: 165-176; Gorman et al., 2003 *Proc BCPC Intl Cong: Crop Science & Technology.* 2: 783-788). The major mechanism of resistance in whitefly to neonicotinoid insecticides appears to be an elevated detoxification capability (Rauch and Nauen, 2003 *Arch Insects Biochem Physiol.* 54: 165-176) and no target-site resistance has been found in neonicotinoid-resistant whitefly populations (Nauen and Denholm, 2005 *Arch Insect Biochem Physiol.* 58:200-215).

Neonicotinoid insecticides remain valuable and effective tools for the management of insect pests in most areas in spite of the limited development of resistance. Control of neonicotinoid-resistant insect pest populations, or for that matter other insecticide-resistant insect pest populations, will rely on the availability of insecticides that are effective on the resistant populations. Preventing or delaying the development of insecticide-resistant insect pest populations also relies on the rotation of insecticides that are not affected by the same resistance mechanisms. In either case, new insecticides that lack cross-resistance to currently available insecticides are imminently needed.

SUMMARY OF THE INVENTION

This invention concerns the discovery of lack of cross-resistance for N-substituted sulfoximine compounds on insect pests that have developed resistance to one or more classes of insecticides including imidacloprid and other neonicotinoids. More particularly, this invention concerns a method to control certain insect pests that have developed resistance to one or more classes of insecticides, including neonicotinoids, organophosphates, carbamates and pyrethroids, which comprises applying to a locus where control is desired an insect-inactivating amount of a compound of the formula (I)

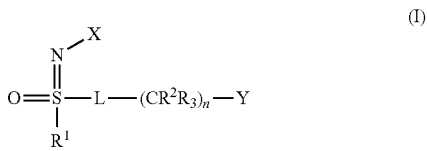

wherein
X represents $NO_2$, CN or $COOR^4$;
L represents a single bond or $R^1$, S and L taken together represent a 5- or 6-membered ring;
$R^1$ represents methyl or ethyl;
$R^2$ and $R^3$ independently represent hydrogen, methyl, ethyl, fluoro, chloro or bromo;
n is an integer from 0-3;
Y represents 6-halopyridin-3-yl, 6-($C_1$-$C_4$)alkylpyridin-3-yl, 6-($C_1$-$C_4$) haloalkylpyridin-3-yl, 6-($C_1$-$C_4$)alkoxypyridin-3-yl, 6-($C_1$-$C_4$)haloalkoxypyridin-3-yl, 2-chlorothiazol-4-yl, or 3-chloroisoxazol-5-yl when n=0-3 and L represents a single bond, or Y represents hydrogen, $C_1$-$C_4$ alkyl, phenyl, 6-halopyridin-3-yl, 6-($C_1$-$C_4$)alkylpyridin-3-yl, 6-($C_1$-$C_4$) haloalkylpyridin-3-yl, 6-($C_1$-$C_4$)alkoxypyridin-3-yl, 6-($C_1$-$C_4$)haloalkoxypyridin-3-yl, 2-chlorothiazol-4-yl, or 3-chloroisoxazol-5-yl when n=0-1 and $R^1$, S and L taken together represent a 5- or 6-membered ring; and
$R^4$ represents $C_1$-$C_3$ alkyl.

Preferred compounds of formula (I) include the following classes:

(1) Compounds of formula (I) wherein X is $NO_2$ or CN, most preferably CN.

(2) Compounds of formula (I) wherein Y represents 6-chloropyridin-3-yl or 6-trifluoromethylpyridin-3-yl having the structure:

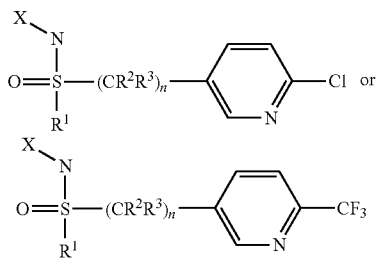

(3) Compounds of formula (I) wherein $R^1$, S and L taken together form a standard 5-membered ring and n=0, i.e., having the structure

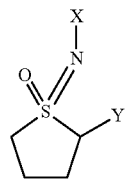

(4) Compounds of formula (I) wherein $R^1$ represents $CH_3$, L represents a single bond and n=1 or 2, most preferably 1, having the structure:

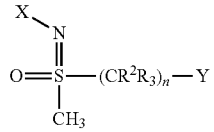

(5) Compounds of formula (I) wherein $R^2$ and $R^3$ independently represent hydrogen, methyl or ethyl.

It will be appreciated by those skilled in the art that the most preferred compounds are generally those which are comprised of combinations of the above preferred classes.

DETAILED DESCRIPTION OF THE INVENTION

Throughout this document, all temperatures are given in degrees Celsius, and all percentages are weight percentages unless otherwise stated.

Unless specifically limited otherwise, the term alkyl (including derivative terms such as alkoxy), as used herein, include straight chain, branched chain, and cyclic groups. Thus, typical alkyl groups are methyl, ethyl, 1-methylethyl, propyl, 1,1-dimethylethyl, and cyclopropyl. The term halogen includes fluorine, chlorine, bromine, and iodine. The term haloalkyl and haloalkoxy includes alkyl and alkoxy groups substituted with from one to the maximum possible number of halogen atoms, preferably fluorine atoms.

The compounds of this invention can exist as one or more stereoisomers. The various stereoisomers include geometric isomers, diastereomers and enantiomers. Thus the compounds of the present invention include racemic mixtures, individual stereoisomers and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials or by conventional resolution procedures.

Methods for the preparation of sulfoximines, other than those described in Scheme H, have been previously disclosed in US Patent Publication 20050228027, whose teachings are incorporated herein.

The compounds of formula (Ia), wherein $R^1$, $R^2$, $R^3$, $R^4$, X, and Y are as previously defined and L is a single bond, can be prepared by the methods illustrated in Scheme A:

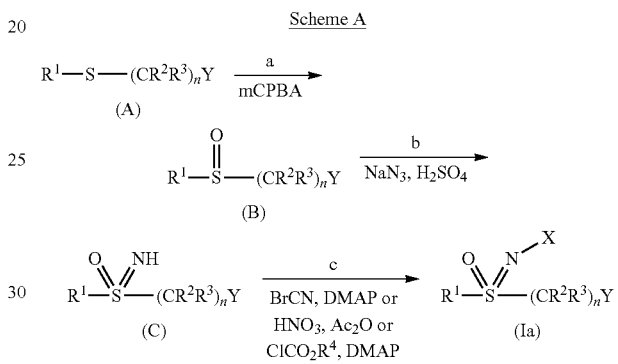

In step a of Scheme A, sulfide of formula (A) is oxidized with meta-chloroperoxybenzoic acid (mCPBA) in a polar solvent below 0° C. to provide sulfoxide of formula (B). In most cases, dichloromethane is the preferred solvent for oxidation.

In step b of Scheme A, sulfoxide (B) is iminated with sodium azide in the presence of concentrated sulfuric acid in an aprotic solvent under heating to provide sulfoximine of formula (C). In most cases, chloroform is the preferred solvent for this reaction.

In step c of Scheme A, the nitrogen of sulfoximine (C) can be either cyanated with cyanogen bromide in the presence of a base, or nitrated with nitric acid in the presence of acetic anhydride under mildly elevated temperature, or carboxylated with alkyl ($R^4$) chloroformate in the presence of base such as 4-dimethylaminopyridine (DMAP) to provide N-substituted sulfoximine (Ia). Base is required for efficient cyanation and carboxylation and the preferred base is DMAP, whereas sulfuric acid is used as catalyst for efficient nitration reaction.

The compounds of formula (Ia), wherein X represents CN and $R^1$, $R^2$, $R^3$, $R^4$ and Y are as previously defined, can be prepared by the mild and efficient method illustrated in Scheme B.

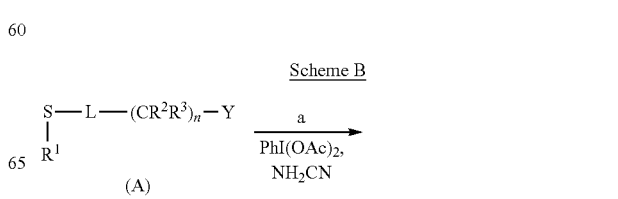

-continued

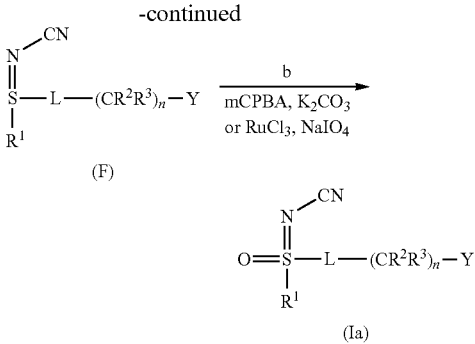

In step a of Scheme B, sulfide is oxidized with iodobenzene diacetate in the presence of cyanamide at 0° C. to give sulfilimine (F). The reaction can be carried out in a polar aprotic solvent like dichloromethane.

In step b of Scheme B, the sulfilimine (F) is oxidized with mCPBA. A base such as potassium carbonate is employed to neutralize the acidity of mCPBA. Protic polar solvents such as ethanol and water are used to increase the solubility of the sulfilimine starting material and the base employed. The sulfilimine (F) can also be oxidized with aqueous sodium or potassium periodinate solution in the presence of catalyst ruthenium trichloride hydrate or similar catalyst. The organic solvent for this catalysis can be polar aprotic solvent such as dichloromethane, chloroform, or acetonitrile.

The α-carbon of the N-substituted sulfoximine of formula (Ia), i.e., n=1, $R^3$=H in the $(CR^2R^3)$ group adjacent to the N-substituted sulfoximine function can be further alkylated or halogenated ($R^5$) in the presence of a base such as potassium hexamethyldisilamide (KHMDS) to give N-substituted sulfoximines of formula (Ib), wherein $R^1$, $R^2$, $R^3$, $R^4$, X, L and Y are as previously defined and Z is an appropriate leaving group, as illustrated in Scheme C. The preferred leaving groups are iodide ($R^5$=alkyl), benzenesulfonimide ($R^5$=F), tetrachloroethene ($R^5$=Cl), and tetrafluoroethene ($R^5$=Br).

Scheme C

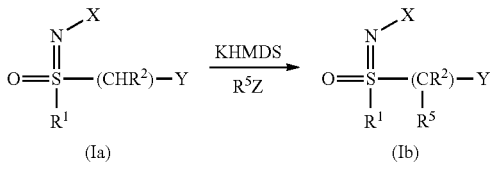

The starting sulfides (A) in Scheme A can be prepared in different ways as illustrated in Schemes D, E, F G, H, and I.

In Scheme D, the sulfide of formula ($A_1$), wherein $R^1$, $R^2$ and Y are as previously defined, n=1, and $R^3$=H, can be prepared from the chloride of formula ($D_1$) by nucleophilic substitution with the sodium salt of an alkyl thiol.

Scheme D

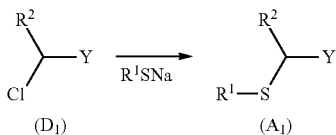

In Scheme E, the sulfide of formula ($A_2$), wherein $R^1$, $R^2$ and Y are as previously defined, n=3, and $R^3$=H, can be prepared from the chloride of formula ($D_2$) by reacting with a 2-mono substituted methyl malonate in the presence of base such as potassium tert-butoxide to provide 2,2-disubstituted malonate, hydrolysis under basic conditions to form a diacid, decarboxylation of the diacid by heating to give a monoacid, reduction of the monoacid with borane-tetrahyrofuran complex to provide an alcohol, tosylation of the alcohol with toluenesulfonyl chloride (tosyl chloride) in the presence of a base like pyridine to give a tosylate and replacement of the tosylate with the sodium salt of the desired thiol.

Scheme E

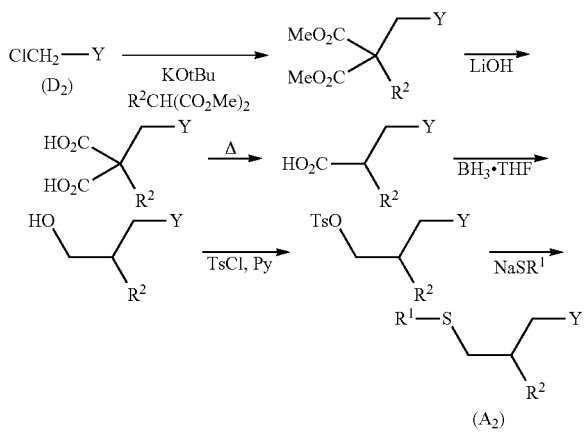

In Scheme F, the sulfide of formula ($A_3$), wherein $R^1$, $R^2$ and Y are as previously defined, n=2, and $R^3$=H, can be prepared from the nitrile of formula (E) by deprotonation with a strong base and alkylation with an alkyl iodide to give α-alkylated nitrile, hydrolysis of the α-alkylated nitrile in the presence of a strong acid like HCl to give an acid, reduction of the acid with borane-tetrahydrofuran complex to provide an alcohol, tosylation of the alcohol with tosyl chloride in the presence of a base like pyridine to give a tosylate and replacement of the tosylate with the sodium salt of the desired thiol.

Scheme F

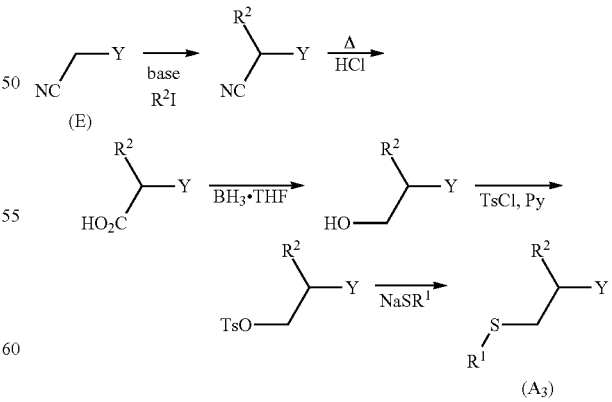

In Scheme G, the sulfide of formula ($A_4$), wherein $R^1$, S and L taken together form a ring, n=0, and Y=isopropyl or phenyl can be prepared from the unsubstituted cyclic sulfide wherein m=0, 1. Chlorination of the cyclic sulfide starting material with N-chlorosuccinimide in benzene followed by alkylation with Grignard reagent can lead to the desired sulfide ($A_4$) in satisfactory yield.

Scheme G

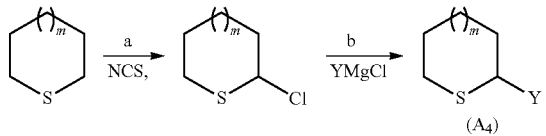

An alternative method for the preparation of sulfides of formula ($A_4$), wherein $R^1$, S and L taken together form a ring, n=0, m=0, and Y=6-halo, 6-($C_1$-$C_4$)alkyl, 6-($C_1$-$C_4$)haloalkyl or 6-($C_1$-$C_4$)alkoxy substituted 3-pyridyl is highlighted in Scheme H. Accordingly, the corresponding appropriately substituted chloromethylpyridine is treated with thiourea, hydrolyzed and subsequently alkylated with 1-bromo-3-chloropropane under aqueous base conditions, and cyclized in the presence of a base like potassium tert-butoxide in a polar aprotic solvent such as tetrahydrofuran (THF).

Scheme H

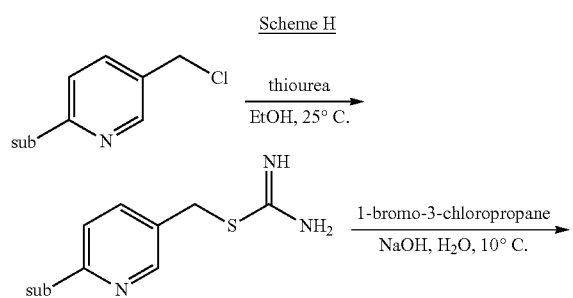

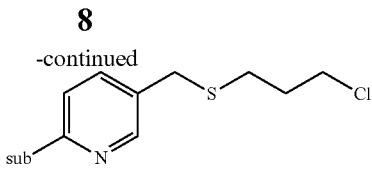

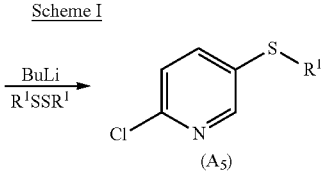

In Scheme I, the sulfide of formula ($A_5$), wherein $R^1$ is previously defined, L is a bond, n=0 and Y is 6-chloropyridin-3-yl can be prepared from 2-chloro-5-bromopyridine with a halo-metal exchange followed by a substitution with disulfide.

Scheme I

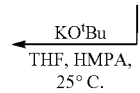

Sulfoximine compounds of type Ib wherein $R^1$, S and L taken together form a saturated 5- or 6-membered ring and n=1 can be prepared by the methods illustrated in Scheme J wherein X and Y are as previously defined and m is 0 or 1.

Scheme J

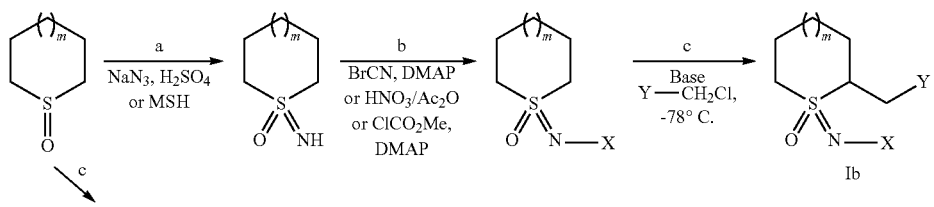

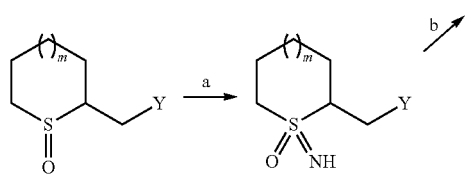

In step a of Scheme J, which is similar to step b of Scheme A, sulfoxide is iminated with sodium azide in the presence of concentrated sulfuric acid or with O-mesitylsulfonylhydroxylamine in a polar aprotic solvent to provide sulfoximine. Chloroform or dichloromethane are the preferred solvents.

In step b of Scheme J, similar to step c of Scheme A, the nitrogen of sulfoximine can be either cyanated with cyanogen bromide, or nitrated with nitric acid followed by treatment with acetic anhydride under refluxing conditions, or carboxylated with methyl chloroformate in the presence of base such as DMAP to provide N-substituted cyclic sulfoximine. Base is required for efficient cyanation and carboxylation and the preferred base is DMAP, whereas sulfuric acid is used as catalyst for efficient nitration reaction.

In step c of Scheme J, the α-carbon of N-substituted sulfoximine can be alkylated with a heteroaromatic methyl halide in the presence of a base such as KHMDS or butyl lithium (BuLi) to give the desired N-substituted sulfoximines. The preferred halide can be bromide, chloride or iodide.

Alternatively, the compounds of formula (Ib) can be prepared by a first α-alkylation of sulfoxides to give α-substituted sulfoxides and then an imination of the sulfoxide followed by N-substitution of the resulting sulfoximine by using the steps c, a and b respectively as described above for Scheme J.

Compounds in which Y represents claimed substituents other than 6-($C_1$-$C_4$) halooalkylpyridin-3-yl and 6-($C_1$-$C_4$) halooalkoxypyridin-3-yl have been disclosed in US Patent Publication 20050228027, whose teachings are incorporated herein.

EXAMPLES

Example I

[(6-Trifluoromethylpyridin-3-yl)methyl](methyl)-oxido-$\lambda^4$-sulfanylidenecyanamide (1)

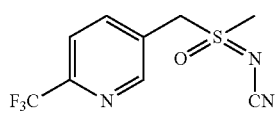

[(6-Trifluoromethylpyridin-3-yl)methyl](methyl)-oxido-$\lambda^4$-sulfanylidenecyanamide (1) was prepared from 3-chloromethyl-6-(trifluoromethyl)pyridine according to the following three step sequence:

(A)

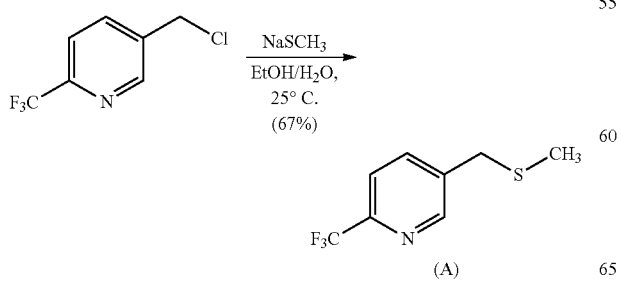

To a solution of 3-chloromethyl-6-(trifluoromethyl)pyridine (5.1 g, 26 mmol) in dimethyl sulfoxide (DMSO; 20 mL) was added in one portion sodium thiomethoxide (1.8 g, 26 mmol). A violent exothermic reaction was observed which resulted in the reaction turning dark. The reaction was stirred for 1 hr, then additional sodium thiomethoxide (0.91 g, 13 mmol) was added slowly. The reaction was stirred overnight, after which it was poured into $H_2O$ and several drops of conc. HCl were added. The mixture was extracted with $Et_2O$ (3×50 mL) and the organic layers combined, washed with brine, dried over $MgSO_4$ and concentrated. The crude product was purified by chromatography (Prep 500, 10% acetone/hexanes) to furnish the sulfide (A) as a pale yellow oil (3.6 g, 67%). $^1$H NMR (300 MHz, $CDCl_3$): δ 8.6 (s, 1H), 7.9 (d, 1H), 7.7 (d, 1H), 3.7 (s, 2H), 2.0 (s, 3H); GC-MS: mass calcd for $C_8H_8F_3NS$ [M]$^+$ 207. Found 207.

(B)

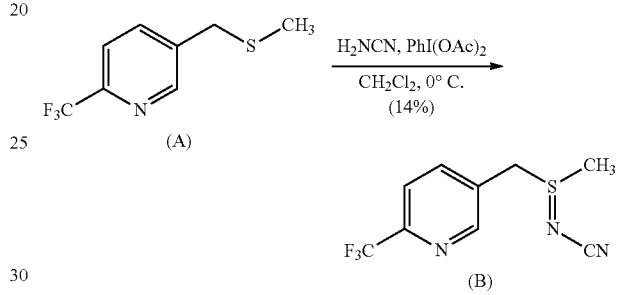

To a solution of sulfide (A) (3.5 g, 17 mmol) and cyanamide (1.4 mg, 34 mmol) in dichloromethane (30 mL) at 0° C. was added iodobenzenediacetate (11.0 g, 34 mmol) all at once. The reaction was stirred for 30 minutes then allowed to warm to room temperature overnight. The mixture was diluted with dichloromethane (50 mL) and washed with $H_2O$. The aqueous layer was extracted with ethyl acetate (4×50 mL), and the combined dichloromethane and ethyl acetate layers dried over $MgSO_4$ and concentrated. The crude product was triturated with hexanes and purified by chromatography (chromatotron, 60% acetone/hexanes) to furnish the sulfilimine (B) as a yellow gum (0.60 g, 14%). IR (film) 3008, 2924, 2143, 1693 cm$^{-1}$; $^1$H NMR (300 MHz, $CDCl_3$): δ 8.8 (s, 1H), 8.0 (d, 1H), 7.8 (d, 1H), 4.5 (d, 1H), 4.3 (d, 1H), 2.9 (s, 3H); LC-MS (ESI): mass calcd for $C_9H_9F_3N_3S$ [M+H]$^+$ 248.04. Found 248.

(C)

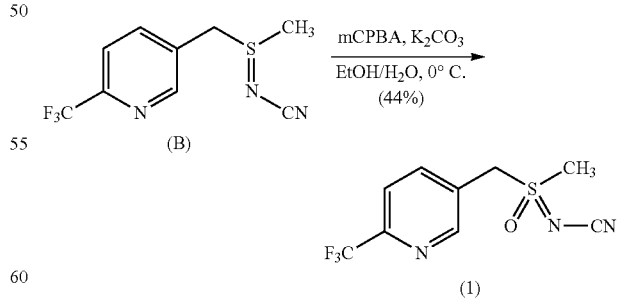

To a solution of m-chloroperbenzoic acid (mCPBA; 80%, 1.0 g, 4.9 mmol) in EtOH (10 mL) at 0° C. was added a solution of $K_2CO_3$ (1.4 g, 10 mmol) in $H_2O$ (7 mL). The solution was stirred for 20 min and then a solution of sulfilimine (B) (0.60 g, 2.4 mmol) in EtOH (20 mL) was added all at once. The reaction was stirred at 0° C. for 30 min, and then allowed to warm to room temperature over the course of 1 hr. The reaction was quenched with aq. sodium bisulfite and the mixture concentrated to remove ethanol. The resulting mixture was extracted with dichloromethane and the combined organic layers dried over MgSO$_4$ and concentrated. The crude product was purified by chromatography (chromatotron, 50% acetone/hexanes) to furnish the sulfoximine (1) as an off-white solid (0.28 g, 44%). Mp=135-137° C.; $^1$H NMR (300 MHz, CDCl$_3$): δ 8.8 (s, 1H), 8.1 (d, 1H), 7.8 (d, 1H), 4.7 (m, 2H), 3.2 (s, 3H); LC-MS (ELSD): mass calcd for C$_9$H$_9$F$_3$N$_3$OS [M+H]$^+$ 264.04. Found 263.92.

Example II

[1-(6-Trifluoromethylpyridin-3-yl)ethyl](methyl)-oxido-2-sulfanylidenecyanamide (2)

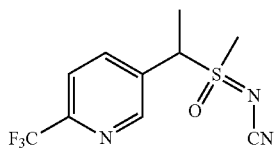

(A)

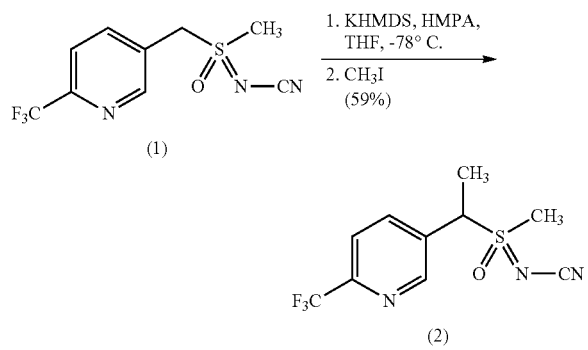

[1-(6-Trifluoromethylpyridin-3-yl)ethyl](methyl)-oxido-λ$^4$-sulfanylidenecyanamide (2) was prepared from [(6-trifluoromethylpyridin-3-yl)methyl]-(methyl)-oxido-λ$^4$-sulfanylidenecyanamide (1) using the method outlined in Scheme C:

To a solution of sulfoximine (1) (50 mg, 0.19 mmol) and hexamethyl-phosphoramide (HMPA; 17 μL, 0.10 mmol) in tetrahydrofuran (THF; 2 mL) at −78° C. was added potassium hexamethyldisilazane (KHMDS; 0.5 M in toluene, 420 μL, 0.21 mmol) dropwise. The solution was stirred at −78° C. for an additional 20 min, after which iodomethane (13 μL, 0.21 mmol) was added. The reaction was allowed to warm to room temperature over the course of 1 hr, after which it was quenched with saturated aqueous (aq.) NH$_4$Cl and extracted with dichloromethane. The organic layer was dried over Na$_2$SO$_4$, concentrated, and the crude product purified by chromatography (chromatotron, 70% acetone/CH$_2$Cl$_2$) to furnish the sulfoximine (2) as a 2:1 mixture of diastereomers (colorless oil; 31 mg, 59%). $^1$H NMR (300 MHz, CDCl$_3$): δ (major diastereomer) 8.8 (s, 1H), 8.1 (d, 1H), 7.8 (d, 1H), 4.6 (q, 1H), 3.0 (s, 3H), 2.0 (d, 3H); (minor diastereomer) 8.8 (s, 1H), 8.1 (d, 1H), 7.8 (d, 1H), 4.6 (q, 1H), 3.1 (s, 3H), 2.0 (d, 3H); LC-MS (ELSD): mass calcd for C$_{10}$H$_{10}$F$_3$N$_3$OS [M+H]$^+$ 278.06. Found 278.05.

Example III 2-(6-Trifluoromethylpyridin-3-yl)-1-oxido-tetrahydro-1H-1λ$^4$-thien-1-ylidenecyanamide (3)

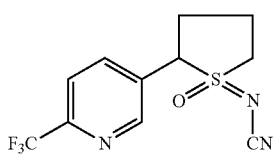

2-(6-Trifluoromethylpyridin-3-yl)-1-oxido-tetrahydro-1H-1λ$^4$-thien-1-ylidene-cyanamide (3) was prepared from 3-chloromethyl-6-(trifluoromethyl)-pyridine according to the 5 step sequence outline below:

(A)

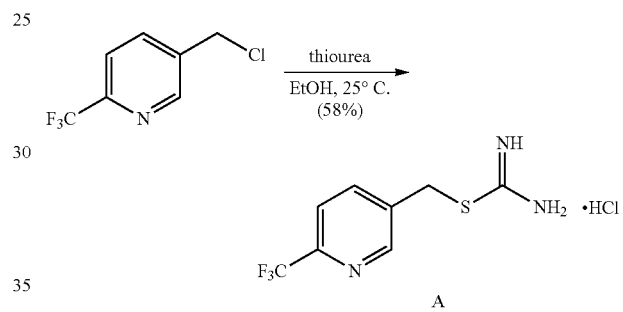

To a suspension of thiourea (1.2 g, 16 mmol) in EtOH (25 mL) was added a solution of 3-chloromethyl-6-(trifluoromethyl)pyridine in EtOH (10 mL). The suspension was stirred at room temperature for 2 days, during which a white precipitated formed. The precipitate was filtered to give the desired amidine hydrochloride as a white solid (2.4 g, 58%). Mp=186-188° C. No further attempt was made to purify the product. $^1$H NMR (300 MHz, CDCl$_3$): δ 8.9 (bs, 4H), 8.4 (s, 1H), 7.6 (d, 1H), 7.3 (d, 1H), 4.2 (s, 2H); LC-MS (ELSD): mass calcd for C$_8$H$_8$F$_3$N$_3$S [M+H]$^+$ 236.05. Found 236.01.

(B)

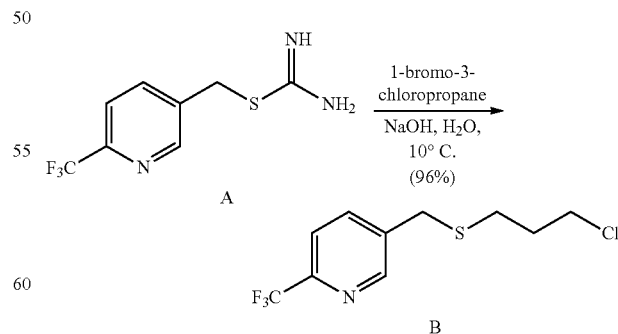

To a solution of amidine hydrochloride (A) (1.8 g, 6.8 mmol) in H$_2$O (12 mL) at 10° C. was added 10 N NaOH (0.68 mL, 6.8 mmol), which resulted in the formation of a white precipitate. The suspension was heated at 100° C. for 30 min, then cooled back down to 10° C. Additional 10 N NaOH (0.68 mL, 6.8 mmol) was added, followed by 1-bromo-3-chloropropane (0.67 mL, 6.8 mmol) all at once. The reaction was stirred at room temperature overnight, then extracted with dichloromethane. The combined organic layers were washed with brine, dried over Na$_2$SO$_4$ and concentrated to furnish the sulfide (B) as a colorless oil (1.7 g, 96%). No further attempt was made to purify the product. $^1$H NMR (300 MHz, CDCl$_3$): δ 8.6 (s, 1H), 7.8 (d, 1H), 7.6 (d, 1H), 3.8 (s, 2H), 3.6 (t, 2H), 2.6 (t, 2H), 2.0 (quint, 2H).

(C)

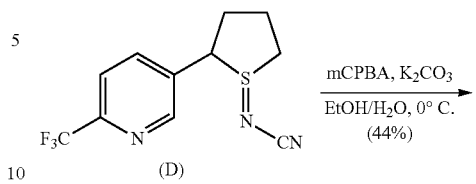

(B)

(C)

To a suspension of potassium tert-butoxide (1.5 g, 13 mmol) in THF (12 mL) was added HMPA (1.7 mL, 10 mmol) followed by a solution of sulfide (B) (1.8 g, 6.7 mmol) in THF (3 mL) dropwise. The reaction was allowed to stir at room temperature overnight, followed by concentration and purification by chromatography (Biotage, 40% EtOAc/hexanes) to furnish cyclized product (C) as an orange oil (230 mg, 15%). $^1$H NMR (300 MHz, CDCl$_3$): δ 8.7 (s, 1H), 8.0 (d, 1H), 7.6 (d, 1H), 4.6 (dd, 1H), 3.2 (m, 1H), 3.1 (m, 1H), 2.5 (m, 1H), 2.3 (m, 1H), 2.1-1.9 (m, 2H).

(D)

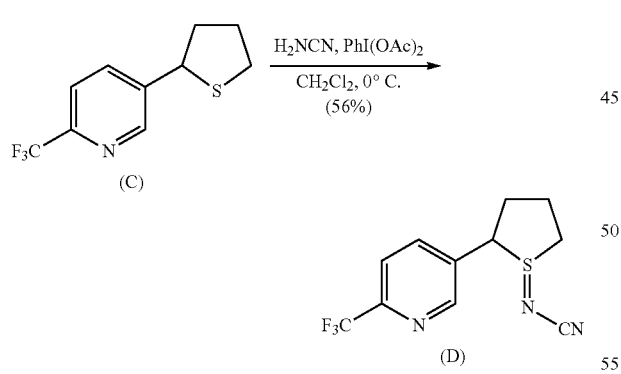

(C)

(D)

To a solution of sulfide (C) (230 mg, 0.99 mmol) and cyanamide (83 mg, 2.0 mmol) in dichloromethane (5 mL) at 0° C. was added iodobenzenediacetate (350 mg, 1.1 mmol) all at once. The reaction was stirred for 3 hr, then concentrated and the crude product purified by chromatography (chromatotron, 50% acetone/hexanes) to furnish the sulfilimine (D) as an orange oil (150 mg, mixture of diastereomers, 56%). $^1$H NMR (300 MHz, CDCl$_3$): δ 8.8 (s, 1H), 7.9 (d, 1H), 7.8 (d, 1H), 4.8 (dd, 1H), 3.5 (m, 2H), 2.9-2.7 (m, 2H), 2.6 (m, 1H), 2.3 (m, 1H).

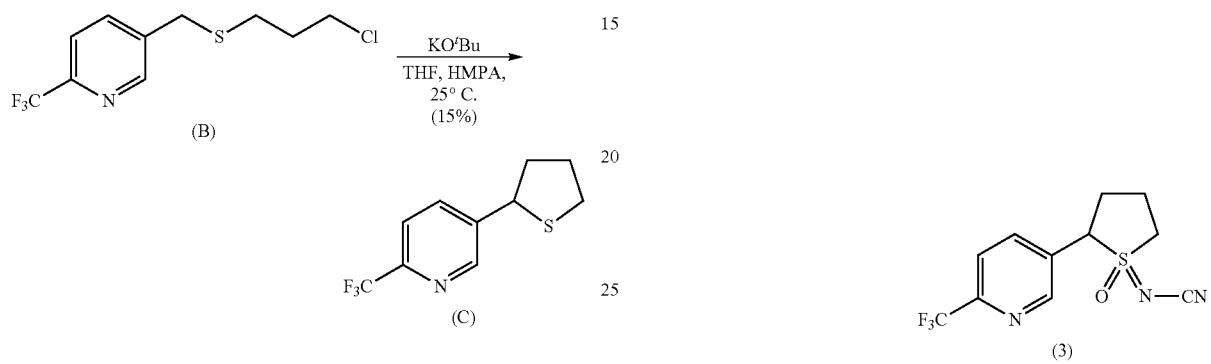

(D)

(3)

To a solution of mCPBA (80%, 180 mg, 0.82 mmol) in EtOH (3 mL) at 0° C. was added a solution of K$_2$CO$_3$ (230 mg, 1.7 mmol) in H$_2$O (1.5 mL). The solution was stirred for 20 min and then a solution of sulfilimine (D) (150 mg, 0.55 mmol) in EtOH (2 mL) was added all at once. The reaction was stirred at 0° C. for 45 min, after which the solvent was decanted into a separate flask and concentrated to give a white solid. The solid was slurried in CHCl$_3$, filtered, and concentrated to furnish pure sulfoximine (3) as a colorless oil (72 mg, 44%). $^1$H NMR (300 MHz, CDCl$_3$): δ (1.5:1 mixture of diastereomers) 8.8 (s, 2H), 8.0 (d, 2H), 7.8 (d, 2H), 4.7 (q, 1H), 4.6 (q, 1H), 4.0-3.4 (m, s, 4H), 3.0-2.4 (m, 8H); LC-MS (ELSD): mass calcd for C$_{11}$H$_{11}$F$_3$N$_3$OS [M+H]$^+$ 290.06. Found 289.99.

Example IV

[1-(6-Chloropyridin-3-yl)methyl](methyl)oxido-λ$^4$-sulfanylidenecyanamide (4)

(4)

[(6-Chloropyridin-3-yl)methyl](methyl)oxido-λ$^4$-sulfanylidenecyanamide (4) was prepared from 3-chloromethyl-6-chloropyridine via the same 3 step sequence outline in Example I. Product was a white solid; mp=115-117° C.; $^1$H NMR (300 MHz, CD$_3$OD/CDCl$_3$) δ 8.5 (d, 1H), 8.0 (dd, 1H), 7.6 (d, 1H), 5.0 (s, 2H), 3.4 (s, 3H); LC-MS (ELSD): mass calcd for $C_8H_9ClN_3OS$ $[M+H]^+$ 230. Found 230.

Example V

[1-(6-Chloropyridin-3-yl)ethyl](methyl)oxido-$\lambda^4$-sulfanylidenecyanamide (5)

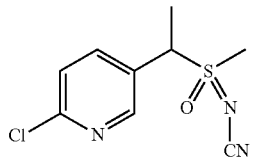

(5)

[1-(6-Chloropyridin-3-yl)ethyl](methyl)oxido-$\lambda^4$-sulfanylidenecyanamide (5) was prepared from [(6-chloropyridin-3-yl)methyl](methyl)oxido-$\lambda^4$-sulfanylidenecyanamide (4) via the same protocol as described in Example II. The final product, isolated as a 3:2 mixture of diastereomers, was an off-white solid; mp=155-164° C. LC-MS (ELSD): mass calcd for $C_9H_9ClN_3OS$ $[M-H]^+$ 242. Found 242. The diastereomers of (5) could be separated by recrystallization (2:1 MeOH/$H_2O$) and subsequent chromatotron chromatography of the supernate to provide (6) and (7) (Stereochemistry arbitrarily assigned).

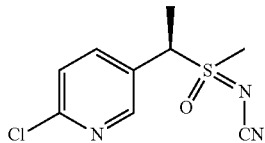

(6)

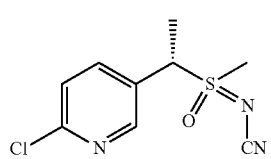

(7)

Compound (6) was isolated as a white solid; mp=163-165° C.; $^1$H NMR (300 MHz, CDCl$_3$): δ 8.4 (d, 1H), 7.9 (dd, 1H), 7.5 (d, 1H), 4.6 (q, 1H), 3.1 (s, 3H), 2.0 (d, 3H); LC-MS (ELSD): mass calcd for $C_9H_{11}ClN_3OS$ $[M+H]^+$, 244. Found 244.

Compound (7) was isolated as a colorless oil; $^1$H NMR (300 MHz, CDCl$_3$) δ 8.4 (d, 1H), 7.9 (dd, 1H), 7.5 (d, 1H), 4.6 (q, 1H), 3.0 (s, 3H), 2.0 (d, 3H); LC-MS (ELSD): mass calcd for $C_9H_{11}ClN_3OS$ $[M+H]^+$, 244. Found 244.

Example VI 2-(6-Chloropyridin-3-yl)-1-oxido-tetrahydro-1H-1$\lambda^4$-thien-1-ylidenecyanamide (8)

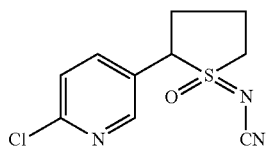

(8)

2-(6-Chloropyridin-3-yl)-1-oxido-tetrahydro-1H-1$\lambda^4$-thien-1-ylidenecyanamide (8) was prepared from 3-chloromethyl-6-chloropyridine according to the same five step sequence described in Example III. Product was a colorless gum and a 1:1 ratio of diastereomers. Diastereomer 1: IR (film) 3439, 3006, 2949, 2194 cm$^{-1}$; $^1$H NMR (300 MHz, CDCl$_3$): δ 8.4 (d, 1H), 7.8 (dd, 1H), 7.4 (d, 1H), 4.6 (dd, 1H), 3.6 (m, 2H), 2.4-2.7 (m, 4H); GC-MS: mass calcd for $C_{10}H_{11}ClN_3OS$ $[M+H]^+$ 256. Found 256. Diastereomer 2: IR (film) 3040, 2926, 2191 cm$^{-1}$; $^1$H NMR (300 MHz, CDCl$_3$): δ 8.4 (d, 1H), 7.8 (dd, 1H), 7.4 (d, 1H), 4.7 (dd, 1H), 3.8 (ddd, 1H), 3.4 (m, 1H), 2.8 (m, 1H), 2.6 (m, 2H), 2.3 (m, 1H); GC-MS: mass calcd for $C_{10}H_{11}ClN_3OS$ $[M+H]^+$ 256. Found 256.

Example VII

Insecticidal Activity of N-Substituted Sulfoximines on a Neonicitinoid-Resistant Q-Biotype *Bemisia tabaci* Strain The insecticidal activity of Compounds 6 and 7 on adults from an insecticide-resistant, Q-biotype *Bemisia tabaci* strain was assessed. The activity of commercial, neonicotinoid insecticides was also assessed and served as the basis for comparisons of relative efficacy on this insecticide-resistant whitefly strain.

The common name associated with the Q-biotype of *B. tabaci* is the sweetpotato whitefly. The strain used in these tests, "CHLORAKA", was collected from cucumbers in Cyprus in 2003 and has exhibited stable and strong resistance to multiple insecticide classes in repeated laboratory testing. Adults from this strain are largely unaffected by exposure to imidacloprid (a neonicotinoid insecticide) at 1000 ppm. The SUD-S strain of *B. tabaci* was the reference strain used in these tests and is a laboratory strain that is fully susceptible to all insecticide groups.

Technical samples of Compounds 6 and 7 were initially dissolved in 90% acetone in distilled water (containing 0.01% Agral) to obtain 5000 ppm stock solutions. Subsequent dilutions were made by using 0.9% acetone in distilled water (containing 0.01% Agral) as the diluent. Commercial formulations of imidacloprid (Confidor, 200SL), thiamethoxam (Actara, 25WG) and acetamiprid (Mospilan, 20SP) were diluted using distilled water containing 0.01% Agral.

Discs cut from fully expanded leaves of cotton (*Gossypium hirsutum* cv. Deltapine 16) were dipped into serial dilutions of insecticide, allowed to air-dry, and placed onto agar-water beds (1%) in plastic Petri dishes. Leaf discs immersed in the diluent only were used for controls. Adult B. tabaci were removed from rearing cages using a motorized aspirator and, after brief narcosis, 20-30 healthy female whiteflies were placed onto each treated leaf disc. Each unit was sealed with a close-fitting, ventilated lid. Once adults had recovered from narcosis, dishes were inverted so that the leaf disc was facing abaxial side down allowing the adult whiteflies to orient normally. All bioassays consisted of three replicates per concentration (including controls). Mortality was assessed at 48 hours after initiation of the test for the commercial standards and at 72 hours for Compounds 6 and 7.

Compounds 6, 7 and the commercial neonicotinoid insecticides imidacloprid, thiamethoxam and acetamiprid were tested in discriminating concentration bioassays against both whitefly strains. More extensive concentration-response bioassays against both whitefly strains were conducted for Compounds 6, 7 and imidacloprid. The data from these more extensive assays were subjected to probit analysis to derive $LC_{50}$ and $LC_{90}$ estimates. Resistance ratios were calculated using the following equation:

$$\text{Resistance Ratio} = \frac{LC_{50} \text{ on Resistant Population}}{LC_{50} \text{ on Susceptible Population}}$$

In the discriminating concentration bioassays, there was only a slight difference in the efficacy of Compounds 6 and 7 on the 2 whitefly strains (Table 1). This was in contrast to the responses for the commercial neonicotinoid insecticides which were much less effective on the CHLORAKA strain compared to the susceptible, reference strain (SUD-S).

TABLE 1

Mortality of adults from an insecticide-resistant Q-biotype B. tabaci strain and a susceptible laboratory strain exposed to discriminating concentrations of Compounds 6, 7, imidacloprid, thiamethoxam, or acetamiprid.

| Compound | Dose | Mortality, S Strain (SUD-S) | Mortality, R Strain (CHLORAKA) |
|---|---|---|---|
| 6 | 40 ppm | 99% | 39% |
|  | 100 ppm | 100% | 79% |
|  | 500 ppm | 100% | 96% |
| 7 | 40 ppm | 98% | 37% |
|  | 100 ppm | 97% | 79% |
|  | 500 ppm | 100% | 97% |
| Imidacloprid | 32 pm | 83% | 2% |
|  | 128 ppm | 95% | 2% |
|  | 4096 ppm | — | 25% |
| Thiamethoxam | 32 ppm | 85% | 0% |
|  | 512 ppm | 94% | 15% |
| Acetamiprid | 32 ppm | 52% | 2% |
|  | 512 ppm | 79% | 30% |

The results from the concentration-response bioassays provided additional documentation of the effectiveness of the N-substituted sulfoximines on neonicotinoid-resistant Q-biotype B. tabaci (Table 2). The similar $LC_{50}$s on the resistant CHLORAKA and susceptible SUD-S strains for Compounds 6 and 7 produced small resistance ratios. This was in contrast to the response for imidacloprid, where a large resistance ratio was obtained due to the high level of resistance observed in the CHLORAKA strain.

TABLE 2

Potency estimates and resistance ratios for Compounds 6, 7 and imidacloprid on an insecticide-resistant, Q-biotype B. tabaci strain and a susceptible laboratory strain.

| Compound | $LC_{50}$, S strain (SUD-S) | $LC_{50}$, R strain (CHLORAKA) | Resistance Ratio |
|---|---|---|---|
| 6 | 7.4 ppm | 45 ppm | 6.1 |
| 7 | 9.0 ppm | 53 ppm | 5.9 |
| Imidacloprid | 4.3 ppm | >4000 ppm* | >930** |

*Accurate calculation of $LC_{50}$ was not possible because doses as high as 4000 ppm caused <50% mortality on the R strain (CHLORAKA).
**Value represents a conservative estimate of the Resistance Ratio calculated using the highest concentration tested as the numerator in the equation.

Example VIII

Insecticidal Activity of N-Substituted Sulfoximines on a Neonicitinoid-Resistant B-Biotype Bemisia tabaci Strain The insecticidal activity of Compound 7 on adults from an insecticide-resistant, B-biotype Bemisia tabaci strain was assessed. The activity of commercial, neonicotinoid insecticides was also assessed and served as the basis for comparisons of relative efficacy on this insecticide-resistant whitefly strain.

The common name associated with the B-biotype of B. tabaci is the silverleaf whitefly. The strain used in these tests, "GUA-MIX", was collected from a variety of crops situated in the Zacapa Valley of Guatemala in January of 2004. This strain exhibits strong resistance to imidacloprid with the majority of adults being largely unaffected by concentrations of 1000 ppm. The SUD-S strain of B. tabaci was the reference strain used in these tests and is a laboratory strain that is fully susceptible to all insecticide groups.

A technical sample of Compound 7 was initially dissolved in 90% acetone in distilled water (containing 0.01% Agral) to obtain a 5000 ppm stock solution. Subsequent dilutions were made by using 0.9% acetone in distilled water (containing 0.01% Agral) as the diluent. Commercial formulations of imidacloprid (Confidor, 200SL), thiamethoxam (Actara, 25WG) and acetamiprid (Mospilan, 20SP) were diluted using distilled water containing 0.01% Agral.

Discs cut from fully expanded leaves of cotton (Gossypium hirsutum cv. Deltapine 16) were dipped into serial dilutions of insecticide, allowed to air-dry, and placed onto agar-water beds (1%) in plastic Petri dishes. Leaf discs immersed in the diluent only were used for controls. Adult B. tabaci were removed from rearing cages using a motorized aspirator and, after brief narcosis, 20-30 healthy female whiteflies were placed onto each treated leaf disc. Each unit was sealed with a close-fitting, ventilated lid. Once adults had recovered from narcosis, dishes were inverted so that the leaf disc was facing abaxial side down allowing the adult whiteflies to orient normally. All bioassays consisted of three replicates per concentration (including controls). Mortality was assessed at 48 hours after initiation of the test for the commercial standards and at 72 hours for Compound 7.

Compound 7 and the commercial neonicotinoid insecticides imidacloprid, thiamethoxam and acetamiprid were tested in discriminating concentration bioassays against both whitefly strains. More extensive concentration-response bioassays against both whitefly strains were conducted for Compound 7 and imidacloprid. The data from these more extensive assays were subjected to probit analysis to derive $LC_{50}$ and $LC_{90}$ estimates. Resistance ratios were calculated using the following equation:

$$\text{Resistance Ratio} = \frac{LC_{50} \text{ on Resistant Population}}{LC_{50} \text{ on Susceptible Population}}$$

In the discriminating concentration bioassays, there was only a slight difference in the efficacy of Compound 7 on the 2 whitefly strains (Table 3). This was in contrast to the responses for the commercial neonicotinoid insecticides, which were much less effective on the GUA-MIX strain compared to the susceptible, reference strain (SUD-S).

TABLE 3

Mortality of adults from an insecticide-resistant B-biotype
B. tabaci strain and a susceptible laboratory strain
exposed to discriminating concentrations of Compound
7, imidacloprid, thiamethoxam, or acetamiprid.

| Compound | Dose | Mortality, S Strain (SUD-S) | Mortality, R Strain (GUA-MIX) |
| --- | --- | --- | --- |
| 7 | 40 ppm | 84% | 70% |
|  | 100 ppm | 95% | 79% |
| Imidacloprid | 32 ppm | 74% | 8% |
|  | 128 ppm | 87% | 39% |
|  | 2048 ppm | — | 49% |
| Thiamethoxam | 25 ppm | — | 10% |
|  | 32 ppm | 57% | — |
|  | 128 ppm | 73% | — |
|  | 250 ppm | — | 51% |
|  | 2500 ppm | — | 87% |
| Acetamiprid | 32 ppm | 65% | 1% |
|  | 512 ppm | 98% | 63% |

The results from the concentration-response bioassays provided additional documentation of the effectiveness of the N-substituted sulfoximine on neonicotinoid-resistant B-biotype B. tabaci (Table 4). The similar $LC_{50}$s on the resistant GUA-MIX and susceptible SUD-S strains for Compound 7 produced a small resistance ratio. This was in contrast to the response for imidacloprid, where a large resistance ratio was obtained due to the high level of resistance observed in the GUA-MIX strain.

TABLE 4

Potency estimates and resistance ratios for Compound 7
and imidacloprid on an insecticide-resistant B-biotype
B. tabaci strain and a susceptible laboratory strain.

| Compound | $LC_{50}$, S strain (SUD-S) | $LC_{50}$, R strain (GUA-MIX) | Resistance Ratio |
| --- | --- | --- | --- |
| 7 | 9.3 ppm | 30.3 ppm | 3.3 |
| Imidacloprid | 11.2 ppm | >500.0 ppm* | >45.5** |

*Accurate calculation of $LC_{50}$ was not possible because doses as high as 2000 ppm caused ~50% mortality on the R strain (GUA-MIX).
**Value represents a conservative estimate of the Resistance Ratio calculated using the highest concentration tested as the numerator in the equation.

Example IX

Insecticidal Activity of N-Substituted Sulfoximines on Insecticide-Resistant Whitefly and Aphid Strains The insecticidal activity of Compounds 2, 4, and 5 on adults from an insecticide-resistant, Q-biotype Bemisia tabaci strain and an insecticide resistant Myzus persicae strain was assessed. Activity was compared to that of commercial insecticides representing major insecticide classes.

The common name associated with the Q-biotype of B. tabaci is the sweetpotato whitefly. The resistant strain used in these tests, "CHLORAKA", was collected from cucumbers in Cyprus in 2003 and has exhibited stable and strong resistance to pyrethroids, organophosphates, and neonicotinoids in repeated laboratory testing. Adults from this strain are largely unaffected by exposure to imidacloprid at 1000 ppm. The SUD-S strain of B. tabaci was the reference strain used in these tests and is a laboratory strain that is fully susceptible to all insecticide groups.

The common name associated with Myzus persicae is the green peach aphid. The resistant M. persicae strain used in these tests, "4013A", was collected from tobacco in Greece in 2000 and is known to possess several resistance mechanisms. The "US1L" strain of M. persicae was the reference strain used in these tests. US1L is fully susceptible to all insecticide groups.

Technical samples of Compounds 2, 4 and 5 were initially diluted in analytical reagent grade acetone to obtain 15,000 ppm stock solutions. Subsequent dilutions used a 10% solution of acetone in distilled water (containing 0.01% Agral®) as the diluent. Commercial formulations of deltamethrin (Decis, 25 g/liter$^{-1}$ EC), dimethoate (Danadim, 400 g/liter$^{-1}$ EC), profenofos (Curacron 500 g/liter$^{-1}$ EC), pirimicarb (Aphox 500 g/liter$^{-1}$ DG) and imidacloprid (Confidor, 200 g/liter$^{-1}$ SL) were obtained by diluting formulated material in distilled water containing a 0.01% concentration of the non-ionic wetter Agral®.

For B. tabaci bioassays, discs cut from fully expanded leaves of cotton (Gossypium hirsutum cv. Deltapine 16) were dipped into serial dilutions of insecticide, allowed to air-dry, and placed onto agar-water (1%) beds in plastic Petri-dishes. Leaf discs immersed in the diluent only were used for controls. Adult B. tabaci were removed from rearing cages using a motorized aspirator and, after brief narcosis, 20-30 healthy female whiteflies were placed onto each treated leaf disc. Each unit was sealed with a close-fitting, ventilated lid. Once adults had recovered from narcosis, dishes were inverted so that the leaf disc was facing abaxial side down allowing the adult whiteflies to orient normally. All bioassays consisted of three replicates per concentration (including controls). Mortality was assessed at 48 hours after initiation of the test for the commercial standards and at 72 hours for Compounds 2, 4, and 5.

For M. persicae bioassays, discs cut from fully expanded leaves of Chinese cabbage (Brassica rapa ssp. Pekinensis cv. Won Bok) plants were dipped into serial dilutions of insecticide, allowed to air-dry, and placed onto agar-water (1%) beds in plastic Petri-dishes. Leaf discs immersed in the diluent only were used for controls. Adults were removed from rearing boxes and, using a fine camel-hair paint brush, 10 healthy, apterous females were placed onto each treated leaf disc and each unit sealed with a close-fitting, ventilated lid. All bioassays consisted of three replicates per dose (including controls). Mortality was scored at 24, 48 and 72 h following initial exposure for all compounds and the 72 h data were used for all analyses.

Mortality data were subjected to probit analysis to derive $LC_{50}$ and $LC_{90}$ estimates. Resistance ratios were calculated using the following equation:

$$\text{Resistance Ratio} = \frac{LC_{50} \text{ on Resistant Population}}{LC_{50} \text{ on Susceptible Population}}$$

The results from the bioassays on whiteflies (*B. tabaci*) demonstrated that the N-substituted sulfoximines were effective on an insecticide resistant strain (Table 5). The similar $LC_{50}$s on the resistant CHLORAKA and susceptible SUD-S strains for Compounds 2, 4, and 5 produced small resistance ratios. This was in contrast to the responses for deltamethrin (a pyrethroid), profenofos (an organophosphate), and imidacloprid (a neonicotinoid), where large resistance ratios were obtained due to the high levels of resistance observed in the CHLORAKA strain.

TABLE 5

Potency estimates and resistance ratios for Compounds 2, 4, and 5 and the commercial insecticides deltamethrin (pyrethroid), profenofos (organophosphate), and imidacloprid (neonicotinoid) on an insecticide-resistant, Q-biotype *B. tabaci* strain and a susceptible laboratory strain.

| Compound | $LC_{50}$, S strain (SUD-S) | $LC_{50}$, R strain (CHLORAKA) | Resistance Ratio |
|---|---|---|---|
| 2 | 1.8 ppm | 5.0 ppm | 2.8 |
| 4 | 3.1 ppm | 16.5 ppm | 5.2 |
| 5 | 4.5 ppm | 13.2 ppm | 2.9 |
| Deltamethrin | 0.4 ppm | 325 ppm | 815 |
| Profenofos | 2.0 ppm | 374 ppm | 189 |
| Imidacloprid | 1.2 ppm | >1000 ppm* | >800** |

*Accurate calculation of $LC_{50}$ was not possible because doses as high as 1000 ppm caused <10% mortality on the R strain (CHLORAKA).
**Value represents a conservative estimate of the Resistance Ratio calculated using the highest concentration tested as the numerator in the equation.

Similar results were obtained from bioassays on aphids (*M. persicae*) in which the N-substituted sulfoximines were effective on an insecticide resistant strain (Table 6). The similar $LC_{50}$s on the resistant 4013A and susceptible US1L strains for Compounds 2, 4, and 5 produced small resistance ratios. This was in contrast to the responses for deltamethrin (a pyrethroid), dimethoate (an organophosphate), pirimicarb (a carbamate), and imidacloprid (a neonicotinoid), where relatively large resistance ratios were obtained due to the high levels of resistance observed in the 4013A strain.

TABLE 6

Potency estimates and resistance ratios for Compounds 2, 4, and 5 and the commercial insecticides deltamethrin (pyrethroid), dimethoate (organophosphate), pirimicarb (carbamate) and imidacloprid (neonicotinoid) on an insecticide-resistant, *Myzus persicae* strain and a susceptible laboratory strain.

| Compound | $LC_{50}$, S strain (US1L) | $LC_{50}$, R strain (4013A) | Resistance Ratio |
|---|---|---|---|
| 2 | 4.13 ppm | 1.52 ppm | 0.4 |
| 4 | 146 ppm | 103 ppm | 0.7 |
| 5 | 62.3 ppm | 12.5 ppm | 0.2 |
| Deltamethrin | 1.5 ppm | 92 ppm | 60 |
| Dimethoate | 46 ppm | 293 ppm | 6.3 |
| Pirimicarb | 14.8 ppm | >1000 ppm* | >60** |
| Imidacloprid | 0.9 | 15.3 | 17 |

*Accurate calculation of $LC_{50}$ was not possible because doses as high as 1000 ppm caused <10% mortality on the R strain (4013A).
**Value represents a conservative estimate of the Resistance Ratio calculated using the highest concentration tested as the numerator in the equation.

Insecticide Utility

The compounds of the invention are useful for the control of insects. Therefore, the present invention also is directed to a method for inhibiting an insect which comprises applying an insect-inhibiting amount of a compound of formula (I) to a locus of the inset, to the area to be protected, or directly on the insect to be controlled. The compounds of the invention may also be used to control other invertebrate pests such as mites, ticks, lice, and nematodes.

The "locus" of insects or other pests is a term used herein to refer to the environment in which the insects or other pests live or where their eggs are present, including the air surrounding them, the food they eat, or objects which they contact. For example, insects which eat, damage or contact edible, commodity, ornamental, turf or pasture plants can be controlled by applying the active compounds to the seed of the plant before planting, to the seedling, or cutting which is planted, the leaves, stems, fruits, grain, and/or roots, or to the soil or other growth medium before or after the crop is planted. Protection of these plants against virus, fungus or bacterium diseases may also be achieved indirectly through controlling sap-feeding pests such as whitefly, plant hopper, aphid and spider mite. Such plants include those which are bred through conventional approaches and which are genetically modified using modern biotechnology to gain insect-resistant, herbicide-resistant, nutrition-enhancement, and/or any other beneficial traits.

It is contemplated that the compounds might also be useful to protect textiles, paper, stored grain, seeds and other foodstuffs, houses and other buildings which may be occupied by humans and/or companion, farm, ranch, zoo, or other animals, by applying an active compound to or near such objects. Domesticated animals, buildings or human beings might be protected with the compounds by controlling invertebrate and/or nematode pests that are parasitic or are capable of transmitting infectious diseases. Such pests include, for example, chiggers, ticks, lice, mosquitoes, flies, fleas and heartworms. Nonagronomic applications also include invertebrate pest control in forests, in yards, along road sides and railroad right of way.

The term "inhibiting an insect" refers to a decrease in the numbers of living insects, or a decrease in the number of viable insect eggs. The extent of reduction accomplished by a compound depends, of course, upon the application rate of the compound, the particular compound used, and the target insect species. At least an inactivating amount should be used. The term "insect-inactivating amount" is used to describe the amount, which is sufficient to cause a measurable reduction in the treated insect population. Generally an amount in the range from about 1 to about 1000 ppm by weight active compound is used. For example, insects and other pests which can be inhibited include, but are not limited to:

Lepidoptera—*Heliothis* spp., *Helicoverpa* spp., *Spodoptera* spp., *Mythimna unipuncta*, *Agrotis ipsilon*, *Earias* spp., *Euxoa auxiliaris*, *Trichoplusia ni*, *Anticarsia gemmatalis*, *Rachiplusia nu*, *Plutella xylostella*, *Chilo* spp., *Scirpophaga incertulas*, *Sesamia inferens*, *Cnaphalocrocis medinalis*, *Ostrinia nubilalis*, *Cydia pomonella*, *Carposina niponensis*, *Adoxophyes orana*, *Archips argyrospilus*, *Pandemis heparana*, *Epinotia aporema*, *Eupoecilia ambiguella*, *Lobesia botrana*, *Polychrosis viteana*, *Pectinophora gossypiella*, *Pieris rapae*, *Phyllonorycter* spp., *Leucoptera malifoliella*, *Phyllocnisitis citrella*

Coleoptera—*Diabrotica* spp., *Leptinotarsa decemlineata*, *Oulema oryzae*, *Anthonomus grandis*, *Lissorhoptrus oryzophilus*, *Agriotes* spp., *Melanotus communis*, *Popillia japonica*, *Cyclocephala* spp., *Tribolium* spp.

Homoptera—*Aphis* spp., *Myzus persicae*, *Rhopalosiphum* spp., *Dysaphis plantaginea*, *Toxoptera* spp., *Macrosiphum euphorbiae*, *Aulacorthum solani*, *Sitobion avenae*, *Metopolophium dirhodum*, *Schizaphis graminum*, *Brachycolus noxius*, *Nephotettix* spp., *Nilaparvata lugens*, *Sogatella furcifera*,

*Laodelphax striatellus, Bemisia tabaci, Trialeurodes vaporariorum, Aleurodes proletella, Aleurothrixus floccosus, Quadraspidiotus perniciosus, Unaspis yanonensis, Ceroplastes rubens, Aonidiella aurantii*

Hemiptera—*Lygus* spp., *Eurygaster maura, Nezara viridula, Piezodorus guildingi, Leptocorisa varicornis, Cimex lectularius, Cimex hemipterus*

Thysanoptera—*Frankliniella* spp., *Thrips* spp., *Scirtothrips dorsalis*

Isoptera—*Reticulitermes flavipes, Coptotermes formosanus, Reticulitermes virginicus, Heterotermes aureus, Reticulitermes hesperus, Coptotermes frenchii, Shedorhinotermes* spp., *Reticulitermes santonensis, Reticulitermes grassei, Reticulitermes banyulensis, Reticulitermes speratus, Reticulitermes hageni, Reticulitermes tibialis, Zootermopsis* spp., *Incisitermes* spp., *Marginitermes* spp., *Macrotermes* spp., *Microcerotermes* spp., *Microtermes* spp.

Diptera—*Liriomyza* spp., *Musca domestica, Aedes* spp., *Culex* spp., *Anopheles* spp., *Fannia* spp., *Stomoxys* spp., Hymenoptera—*Iridomyrmex humilis, Solenopsis* spp., *Monomorium pharaonis, Atta* spp., *Pogonomyrmex* spp., *Camponotus* spp., *Monomorium* spp., *Tapinoma sessile, Tetramorium* spp., *Xylocapa* spp., *Vespula* spp., *Polistes* spp.

Mallophaga (chewing lice)

Anoplura (sucking lice)—*Pthirus pubis, Pediculus* spp.

Orthoptera (grasshoppers, crickets)—*Melanoplus* spp., *Locusta migratoria, Schistocerca gregaria, Gryllotalpidae* (mole crickets).

Blattoidea (cockroaches)—*Blatta orientalis, Blattella germanica, Periplaneta americana, Supella longipalpa, Periplaneta australasiae, Periplaneta brunnea, Parcoblatta pennsylvanica, Periplaneta fuliginosa, Pycnoscelus surinamensis,*

Siphonaptera—*Ctenophalides* spp., *Pulex irritans*

Acari—*Tetranychus* spp., *Panonychus* spp., *Eotetranychus carpini, Phyllocoptruta oleivora, Aculus pelekassi, Brevipalpus phoenicis, Boophilus* spp., *Dermacentor variabilis, Rhipicephalus sanguineus, Amblyomma americanum, Ixodes* spp., *Notoedres cati, Sarcoptes scabiei, Dermatophagoides* spp.

Nematoda—*Dirofilaria immitis, Meloidogyne* spp., *Heterodera* spp., *Hoplolaimus columbus, Belonolaimus* spp., *Pratylenchus* spp., *Rotylenchus reniformis, Criconemella ornata, Ditylenchus* spp., *Aphelenchoides besseyi, Hirschmanniella* spp.

Compositions

The compounds of this invention are applied in the form of compositions which are important embodiments of the invention, and which comprise a compound of this invention and a phytologically-acceptable inert carrier. Control of the pests is achieved by applying compounds of the invention in forms of sprays, topical treatment, gels, seed coatings, microcapsulations, systemic uptake, baits, eartags, boluses, foggers, fumigants aerosols, dusts and many others. The compositions are either concentrated solid or liquid formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations from 10 ppm to 5000 ppm by weight of compound are expected to provide good control. With many of the compounds, concentrations from 100 to 1500 ppm will suffice.

The locus to which a compound is applied can be any locus inhabited by an insect or mite, for example, vegetable crops, fruit and nut trees, grape vines, ornamental plants, domesticated animals, the interior or exterior surfaces of buildings, and the soil around buildings.

Because of the unique ability of insect eggs to resist toxicant action, repeated applications may be desirable to control newly emerged larvae, as is true of other known insecticides and acaricides.

Systemic movement of compounds of the invention in plants may be utilized to control pests on one portion of the plant by applying the compounds to a different portion of it. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal toxins, those expressing herbicide resistance, such as "Roundup Ready®" seed, or those with "stacked" foreign genes expressing insecticidal toxins, herbicide resistance, nutrition-enhancement and/or other beneficial traits.

An insecticidal bait composition consisting of compounds of the present invention and attractants and/or feeding stimulants may be used to increase efficacy of the insecticides against insect pest in a device such as trap, bait station, and the like. The bait composition is usually a solid, semi-solid (including gel) or liquid bait matrix including the stimulants and one or more non-microencapsulated or microencapsulated insecticides in an amount effective to act as kill agents.

The compounds of the present invention (Formula I) are often applied in conjunction with one or more other insecticides or fungicides or herbicides to obtain control of a wider variety of pests diseases and weeds. When used in conjunction with other insecticides or fungicides or herbicides, the presently claimed compounds can be formulated with the other insecticides or fungicides or herbicide, tank mixed with the other insecticides or fungicides or herbicides, or applied sequentially with the other insecticides or fungicides or herbicides.

Some of the insecticides that can be employed beneficially in combination with the compounds of the present invention include: antibiotic insecticides such as allosamidin and thuringiensin; macrocyclic lactone insecticides such as spinosad, spinetoram, and other spinosyns including the 21-butenyl spinosyns and their derivatives; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; biological insecticides such as *Bacillus popilliae, B. sphaericus, B. thuringiensis* subsp. *aizawai, B. thuringiensis* subsp. *kurstaki, B. thuringiensis* subsp. *tenebrionis, Beauveria bassiana, Cydia pomonella* granulosis virus, Douglas fir tussock moth NPV, gypsy moth NPV, *Helicoverpa zea* NPV, Indian meal moth granulosis virus, *Metarhizium anisopliae, Nosema locustae, Paecilomyces fumosoroseus, P. lilacinus, Photorhabdus luminescens, Spodoptera exigua* NPV, trypsin modulating oostatic factor, *Xenorhabdus nematophilus*, and *X. bovienii*, plant incorporated protectant insecticides such as Cry1Ab, Cry1Ac, Cry1F, Cry1A.105, Cry2Ab2, Cry3A, mir Cry3A, Cry3Bb1, Cry34, Cry35, and VIP3A; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methyl-chloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, imicyafos, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spirodiclofen, spiromesifen and spirotetramat; thiourea insecticides such as diafenthiuron; urea insecticides such as flucofuron and sulcofuron; and unclassified insecticides such as AKD-3088, chlorantraniliprole, closantel, crotamiton, cyflumetofen, E2Y45, EXD, fenazaflor, fenazaquin, fenoxacrim, fenpyroximate, FKI-1033, flubendiamide, HGW86, hydramethylnon, IKI-2002, isoprothiolane, malonoben, metaflumizone, metoxadiazone, nifluridide, NNI-9850, NNI-0101, pymetrozine, pyridaben, pyridalyl, pyrifluquinazon, Qcide, rafoxanide, Rynaxypyr™, SYJ-159, triarathene and triazamate and any combinations thereof.

Some of the fungicides that can be employed beneficially in combination with the compounds of the present invention include: 2-(thiocyanatomethylthio)-benzothiazole, 2-phenylphenol, 8-hydroxyquinoline sulfate, Ampelomyces, quisqualis, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, kasugamycin, kasugamycin hydrochloride hydrate, kresoxim-methyl, mancopper, mancozeb, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyributicarb, pyrifenox, pyrimethanil, pyroquilon, quinoclamine, quinoxyfen, quintozene, Reynoutria sachalinensis extract, silthiofam, simeconazole, sodium 2-phenylphenoxide, sodium bicarbonate, sodium pentachlorophenoxide, spiroxamine, sulfur, SYP-Z071, tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, *Candida oleophila, Fusarium oxysporum, Gliocladium* spp., *Phlebiopsis gigantean, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, and any combinations thereof.

Some of the herbicides that can be employed in conjunction with the compounds of the present invention include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flampropand flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquati, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, fluorochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac.

We claim:

1. A method comprising applying an insect-inactivating amount of a compound selected from the group consisting of compounds (5), (6) and (7)

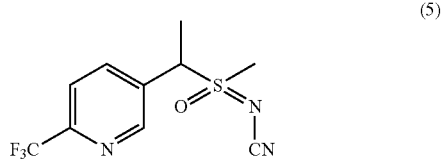 [SMILES: CC(c1ccc(C(F)(F)F)nc1)S(C)(=O)=NC#N]

(5)

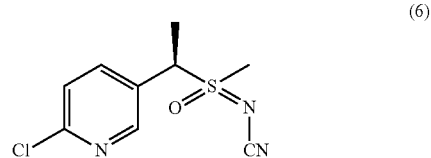

(6)

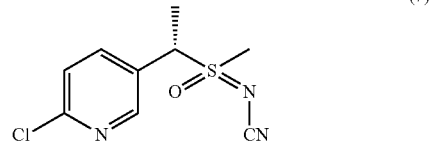

(7)

to a locus where control of insects is desired
wherein said insects are *Bemisia tabaci* that are resistant to one or more insecticides selected from the group consisting of imidacloprid, thiamethoxam, and acetamiprid, and
wherein said insects are known to be resistant to one or more insecticides selected from the group consisting of imidacloprid, thiamethoxam, and acetamiprid.

2. A method comprising applying an insect-inactivating amount of compound (2)

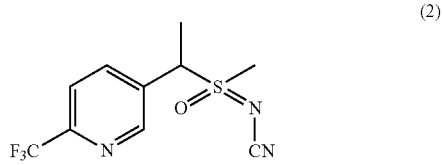

(2)

to a locus where control of insects is desired
wherein said insects are *Bemisia tabaci* that are resistant to one or more insecticides selected from the group consisting of deltamethrin, profenofosm, and imidacloprid, and
wherein said insects are known to be resistant to one or more insecticides selected from the group consisting of deltamethrin, profenofosm, and imidacloprid.

* * * * *